United States Patent
Nomura et al.

(10) Patent No.: US 12,140,553 B2
(45) Date of Patent: Nov. 12, 2024

(54) IMAGE PROCESSING APPARATUS, RADIOGRAPHY SYSTEM, IMAGE PROCESSING METHOD, AND IMAGE PROCESSING PROGRAM

(71) Applicant: FUJIFILM Corporation, Tokyo (JP)

(72) Inventors: Kengo Nomura, Tokyo (JP); Yasunori Narukawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 333 days.

(21) Appl. No.: 17/462,274

(22) Filed: Aug. 31, 2021

(65) Prior Publication Data

US 2021/0396687 A1 Dec. 23, 2021

Related U.S. Application Data

(63) Continuation of application No. PCT/JP2019/041927, filed on Oct. 25, 2019.

(30) Foreign Application Priority Data

Mar. 29, 2019 (JP) .................................. 2019-069076

(51) Int. Cl.
*G01N 23/04* (2018.01)
*A61B 6/00* (2024.01)
(Continued)

(52) U.S. Cl.
CPC ............ *G01N 23/04* (2013.01); *G01N 23/083* (2013.01); *G01N 23/18* (2013.01); *G06T 5/70* (2024.01);
(Continued)

(58) Field of Classification Search
CPC ....... G01N 2223/401; G01N 2223/628; G01N 2223/629; G01N 23/04; G01N 23/083;
(Continued)

(56) References Cited

U.S. PATENT DOCUMENTS 6,377,654 B1 * 4/2002 Willems ............... G01B 15/025
378/54
6,466,643 B1 * 10/2002 Bueno ..................... G01N 23/04
378/58
(Continued)

FOREIGN PATENT DOCUMENTS

CN 102577356 A 7/2012
CN 104685374 A 6/2015
(Continued)

OTHER PUBLICATIONS

Office Action issued May 24, 2022 in Japanese Application No. 2021-511088.
(Continued)

*Primary Examiner* — Dani Fox
*Assistant Examiner* — Soorena Kefayati
(74) *Attorney, Agent, or Firm* — Sughrue Mion, PLLC

(57) ABSTRACT

Provided are an image processing apparatus, a radiography system, an image processing method, and an image processing program by which a radiographic image can be accurately corrected. An image processing apparatus includes an image acquisition unit that acquires, from a radiation detector in which a plurality of pixels each of which outputs an electrical signal according to a dose of radiation R emitted from a radiation source are arranged, a radiographic image captured in a state in which end parts of the radiation detector overlap with each other; and a correction unit that corrects an influence of the end portion on a far side from the radiation source, which is included in the radiographic image.

13 Claims, 6 Drawing Sheets

(51) Int. Cl.
  *G01N 23/083* (2018.01)
  *G01N 23/18* (2018.01)
  *G06T 5/70* (2024.01)

(52) U.S. Cl.
  CPC ...... *A61B 6/5282* (2013.01); *G01N 2223/401* (2013.01); *G01N 2223/629* (2013.01); *G06T 2207/10116* (2013.01)

(58) Field of Classification Search
  CPC .......... G01N 23/18; G06T 2207/10116; G06T 2207/30136; G06T 5/002; G06T 7/0004; G06T 5/70; G06T 5/80; G06T 5/94; G06T 5/00; A61B 6/5241; A61B 6/542; A61B 6/585; A61B 6/4266; A61B 6/524; A61B 6/5282; G01T 1/171; G01T 1/20; G01T 7/005
  See application file for complete search history.

(56) References Cited

U.S. PATENT DOCUMENTS

| | | | | |
|---|---|---|---|---|
| 6,714,680 B1* | 3/2004 | Sasada | ...................... | G06T 7/32 |
| | | | | 382/284 |
| 9,109,998 B2* | 8/2015 | Nathaniel | .............. | G01N 23/04 |
| 9,151,721 B2* | 10/2015 | Safai | ..................... | G01N 23/203 |
| 2002/0154811 A1* | 10/2002 | Katsuta | .................. | G01N 21/91 |
| | | | | 348/125 |
| 2003/0035576 A1* | 2/2003 | Roder | .................. | G06T 7/0004 |
| | | | | 382/145 |
| 2003/0058991 A1* | 3/2003 | Lott | ....................... | G01N 23/04 |
| | | | | 378/60 |
| 2004/0101109 A1* | 5/2004 | Shih | ........................ | G06T 7/001 |
| | | | | 378/207 |
| 2006/0067461 A1* | 3/2006 | Yin | ............................ | G06T 5/10 |
| | | | | 378/5 |
| 2006/0131496 A1* | 6/2006 | Fitzgerald | ............. | G01F 23/288 |
| | | | | 250/356.1 |
| 2008/0152084 A1* | 6/2008 | Safai | ...................... | G01N 23/04 |
| | | | | 378/63 |
| 2008/0267345 A1* | 10/2008 | Nagumo | .............. | G01N 23/046 |
| | | | | 378/11 |
| 2011/0168900 A1* | 7/2011 | Dobbs | .................... | G01M 11/00 |
| | | | | 250/360.1 |
| 2011/0274237 A1* | 11/2011 | Muenker | .............. | G01N 23/044 |
| | | | | 378/4 |
| 2011/0293164 A1* | 12/2011 | Sato | ..................... | A61B 6/5264 |
| | | | | 382/132 |
| 2012/0219203 A1 | 8/2012 | Adachi | | |
| 2012/0312995 A1* | 12/2012 | Morf | ................. | H01L 27/14663 |
| | | | | 250/363.01 |
| 2012/0312997 A1 | 12/2012 | Iwakiri et al. | | |
| 2013/0142306 A1* | 6/2013 | Okuno | ................. | A61B 6/4452 |
| | | | | 378/62 |
| 2013/0287288 A1* | 10/2013 | Bendall | ................. | G06T 7/0004 |
| | | | | 382/154 |
| 2014/0326705 A1* | 11/2014 | Kodama | .............. | B23K 26/042 |
| | | | | 219/121.83 |
| 2015/0192684 A1 | 7/2015 | Ito | | |
| 2015/0235357 A1* | 8/2015 | Nagashima | .......... | G01B 15/025 |
| | | | | 382/141 |
| 2015/0245807 A1* | 9/2015 | Tajima | ................. | A61B 6/5294 |
| | | | | 378/98 |
| 2015/0247936 A1* | 9/2015 | Gemma | .................... | G01T 1/20 |
| | | | | 250/363.01 |
| 2015/0251018 A1* | 9/2015 | Tajima | ..................... | G06T 5/70 |
| | | | | 378/28 |
| 2016/0320282 A1* | 11/2016 | Dingman | ................. | G01N 9/24 |
| 2017/0061598 A1* | 3/2017 | Nagashima | ............. | G06T 7/001 |
| 2017/0106215 A1 | 4/2017 | Boutry-Duthil | | |
| 2017/0122878 A1* | 5/2017 | Ono | ..................... | G01B 11/245 |
| 2017/0186174 A1* | 6/2017 | George | ..................... | G06T 7/12 |
| 2017/0296133 A1* | 10/2017 | Katsumata | ............... | A61B 6/50 |
| 2018/0108118 A1* | 4/2018 | Takahashi | ........... | A61B 6/5235 |
| 2019/0079031 A1* | 3/2019 | Safai | .................... | G01N 29/043 |
| 2019/0302038 A1* | 10/2019 | Safai | ............... | G01N 23/20008 |
| 2020/0268326 A1* | 8/2020 | Erler | ..................... | A61B 6/4266 |

FOREIGN PATENT DOCUMENTS

| | | |
|---|---|---|
| JP | 2009-201552 A | 9/2009 |
| JP | 2009-201586 A | 9/2009 |
| JP | 2012-251978 A | 12/2012 |
| JP | 2013-135390 A | 7/2013 |
| JP | 2014-095623 A | 5/2014 |
| JP | 2014-102202 A | 6/2014 |
| JP | 2015-165846 A | 9/2015 |
| JP | 2017-051867 A | 3/2017 |
| JP | 2017-516610 A | 6/2017 |
| JP | 2017-189393 A | 10/2017 |
| JP | 2017-209517 A | 11/2017 |

OTHER PUBLICATIONS

International Search Report dated Jan. 21, 2020, issued by the International Searching Authority in application No. PCT/JP2019/041927.
Written Opinion dated Jan. 21, 2020, issued by the International Searching Authority in application No. PCT/JP2019/041927.
International Preliminary Report on Patentability dated Sep. 28, 2021, issued by the International Bureau in application No. PCT/JP2019/041927.
Chinese Office Action dated Aug. 10, 2023 in Application No. 201980094253.0.
Chinese Office Action dated Dec. 1, 2023 in App. No. 201980094253.0.
Office Action issued Feb. 24, 2024 in Chinese Application No. 201980094253.0.

* cited by examiner

IMAGE PROCESSING APPARATUS, RADIOGRAPHY SYSTEM, IMAGE PROCESSING METHOD, AND IMAGE PROCESSING PROGRAM

CROSS-REFERENCE TO RELATED APPLICATIONS

This application is a Continuation of PCT International Application No. PCT/JP2019/041927 filed on Oct. 25, 2019, which claims priority under 35 U.S.C § 119(a) to Japanese Patent Application No. 2019-069076 filed on Mar. 29, 2019. Each of the above application(s) is hereby expressly incorporated by reference, in its entirety, into the present application.

BACKGROUND OF THE INVENTION

1. Field of the Invention

The present disclosure relates to an image processing apparatus, a radiography system, an image processing method, and an image processing program.

2. Description of the Related Art

In the related art, non-destructive inspection using radiation has been performed. As a technique related to the non-destructive inspection, disclosed is a technique of emitting radiation from a radiation source in a state in which a radiation detection medium is wound around the outer periphery of a welded portion of a pipe to be inspected and the radiation source is disposed on the central axis of the pipe, and acquiring a radiographic image generated by the radiation detection medium (see JP2014-102202A). In the technique described in JP2014-102202A, since the radiation detection medium is wound around the pipe, the end parts of the radiation detection medium overlap with each other.

Meanwhile, JP2017-189393A describes a technique of correcting an appearance region due to the appearance of a radiation detection device, which detects radiation, on a close side to the radiation source in an overlapping portion in which a plurality of the radiation detection devices overlap with each other, for a radiographic image captured in a state in which the radiation detection devices are arranged to overlap with each other.

SUMMARY OF THE INVENTION

In a case where the technique described in JP2017-189393A is applied to the technique of JP2014-102202A and the radiographic image in the overlapping portion in which the end parts of the radiation detection medium overlap with each other is corrected, the radiographic image cannot be sufficiently corrected and the correction accuracy may be poor. In a case where the correction accuracy is poor, the image quality of the corrected radiographic image deteriorates.

The present disclosure has been made in view of the above circumstances, and an object thereof is to provide an image processing apparatus, a radiography system, an image processing method, and an image processing program by which a radiographic image can be accurately corrected.

In order to achieve the above object, an image processing apparatus according to a first aspect of the present disclosure comprises: an image acquisition unit that acquires, from a radiation detector in which a plurality of pixels each of which outputs an electrical signal according to a dose of radiation emitted from a radiation source are arranged, a radiographic image captured in a state in which end parts of the radiation detector overlap with each other; and a correction unit that corrects an influence of the end part on a far side from the radiation source, which is included in the radiographic image.

In the image processing apparatus according to a second aspect of the present disclosure, in the image processing apparatus according to the first aspect, the influence is an influence of backscattered radiation caused by the end part on the far side.

In the image processing apparatus according to a third aspect of the present disclosure, in the image processing apparatus according to the first or second aspect, the correction unit corrects the influence on an image of an overlapping portion of the end parts of the radiation detector, in the radiographic image.

In addition, the image processing apparatus according to a fourth aspect of the present disclosure, in the image processing apparatus according to any one of the first to third aspects, further comprises a correction coefficient acquisition unit that acquires a correction coefficient obtained on the basis of a correction image captured by the radiation detector in a state of absence of a subject, after variation in sensitivity of the plurality of pixels of the radiation detector is corrected on the basis of a sensitivity correction image captured by the radiation detector in a state of the absence of the subject, in which the correction unit corrects the radiographic image acquired by the image acquisition unit, by using the correction coefficient.

Alternatively, in the image processing apparatus according to a fifth aspect of the present disclosure, in the image processing apparatus according to any one of the first to third aspects, the radiographic image that the image acquisition unit acquires is a radiographic image in which a portion to be inspected of an object to be inspected is imaged, the image processing apparatus further comprises a correction coefficient acquisition unit that acquires a correction coefficient obtained on the basis of a correction image in which a portion of the object to be inspected different from the portion to be inspected is imaged by the radiation detector, and the correction unit corrects the radiographic image acquired by the image acquisition unit, by using the correction coefficient.

Further, in the image processing apparatus according to a sixth aspect of the present disclosure, in the image processing apparatus according to the fourth or fifth aspect, the correction coefficient acquisition unit derives the correction coefficient, on the basis of a pixel value of an image of an overlapping portion of the end parts of the radiation detector and a pixel value of an image of a non-overlapping portion of the radiation detector in the correction image.

In the image processing apparatus according to a seventh aspect of the present disclosure, in the image processing apparatus according to any one of the first to sixth aspects, the radiation detector is flexible, and the image acquisition unit acquires the radiographic image captured, in a state in which the radiation detector is bent and one end part and the other end part of the radiation detector overlap with each other.

In the image processing apparatus according to an eighth aspect of the present disclosure, in the image processing apparatus according to any one of the first to sixth aspects, the image acquisition unit acquires the radiographic image captured by each of a plurality of the radiation detectors arranged in a state in which the end parts overlap with each other.

Further, a radiography system according to a ninth aspect of the present disclosure comprises a radiation detector in which a plurality of pixels each of which outputs an electrical signal according to a dose of emitted radiation are arranged; and the image processing apparatus according to the present disclosure.

In the radiography system according to a tenth aspect of the present disclosure, in the radiography system according to the ninth aspect, each of the plurality of pixels includes a conversion element that generates a larger amount of electric charge as the dose of emitted radiation becomes larger, and a switching element that outputs the electric charge generated by the conversion element as the electrical signal.

Further, an image processing method according to an eleventh aspect of the present disclosure comprises: acquiring, from a radiation detector in which a plurality of pixels each of which outputs an electrical signal according to a dose of radiation emitted from a radiation source are arranged, a radiographic image captured in a state in which end parts of the radiation detector overlap with each other; and correcting an influence of the end part on a far side from the radiation source, which is included in the radiographic image.

Further, an image processing program according to a twelfth aspect of the present disclosure is a program that causes a computer to execute a process comprising: acquiring, from a radiation detector in which a plurality of pixels each of which outputs an electrical signal according to a dose of radiation emitted from a radiation source are arranged, a radiographic image captured in a state in which end parts of the radiation detector overlap with each other; and correcting an influence of the end part on a far side from the radiation source, which is included in the radiographic image.

Further, an image processing apparatus according to the present disclosure is an image processing apparatus having a processor and a memory, and the processor acquires, from a radiation detector in which a plurality of pixels each of which outputs an electrical signal according to a dose of radiation emitted from a radiation source are arranged, a radiographic image captured in a state in which end parts of the radiation detector overlap with each other, and corrects an influence of the end part on a far side from the radiation source, which is included in the radiographic image.

According to the present disclosure, the radiographic image can be accurately corrected.

DESCRIPTION OF THE PREFERRED EMBODIMENTS

Hereinafter, an exemplary embodiment of the technique according to the present disclosure will be described in detail with reference to the drawings.

Figure 1:
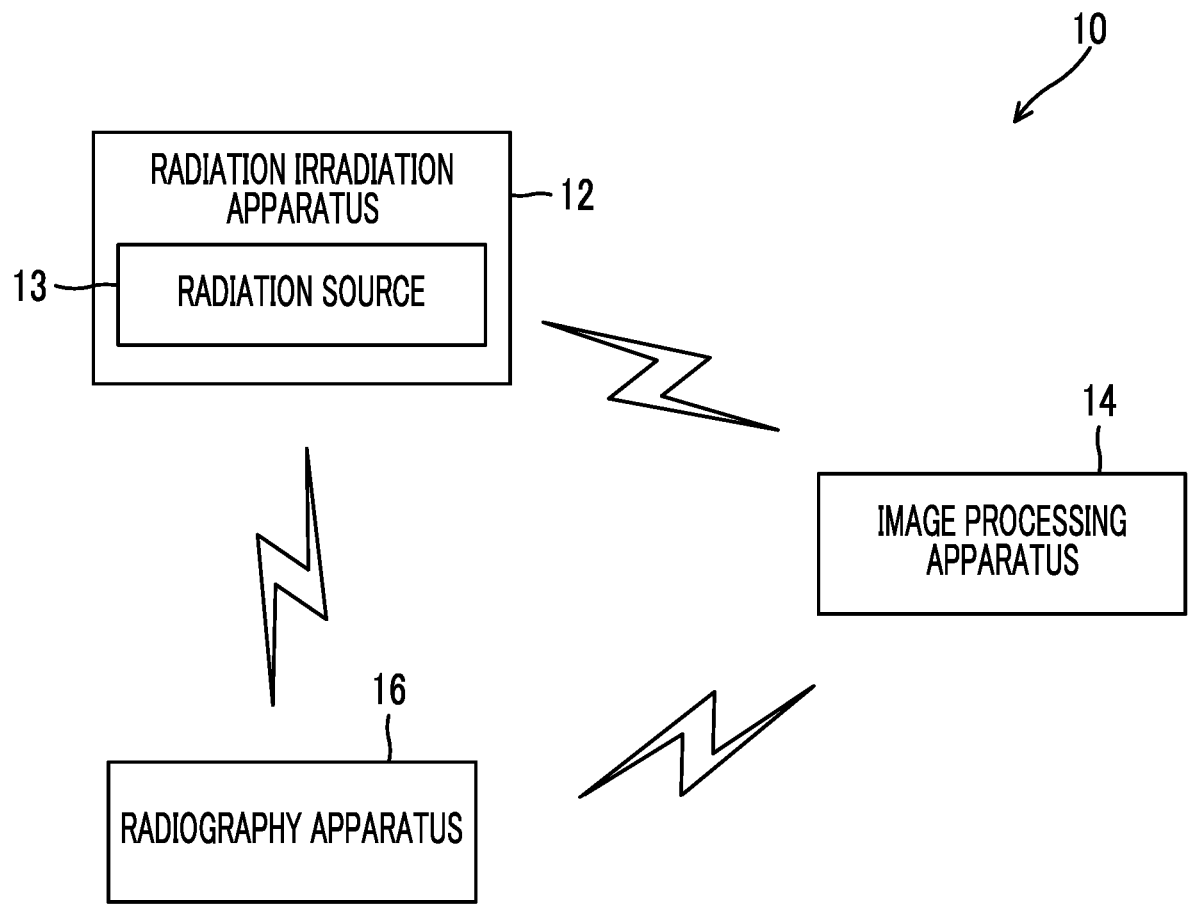
FIG. 1 is a block diagram showing an example of a configuration of a radiography system of an embodiment.

First, the configuration of a radiography system 10 that is used in the non-destructive inspection of the present embodiment will be described with reference to FIG. 1. As shown in FIG. 1, the radiography system 10 comprises a radiation irradiation apparatus 12, an image processing apparatus 14, and a radiography apparatus 16. Examples of the image processing apparatus 14 include a mobile terminal, such as a laptop computer.

The radiation irradiation apparatus 12 comprises a radiation source 13 that emits radiation, such as X-rays. The radiation irradiation apparatus 12, the image processing apparatus 14, and the radiography apparatus 16 can transmit and receive information to and from one another through wireless communication.

Figure 2:
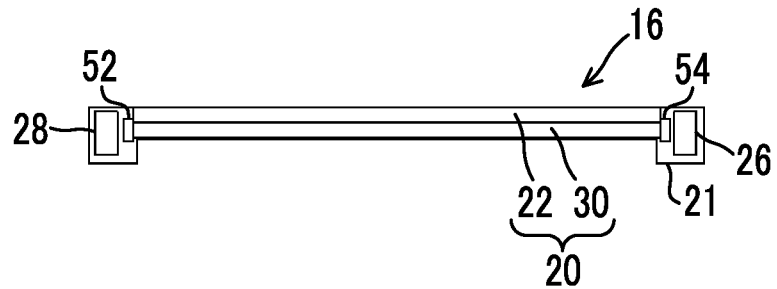
FIG. 2 is a side cross-sectional view showing an example of a configuration of a radiography apparatus of the embodiment.

Next, the configuration of the radiography apparatus 16 of the present embodiment will be described with reference to FIG. 2. As shown in FIG. 2, the radiography apparatus 16 comprises a housing 21 through which radiation is transmitted, and a radiation detector 20 that detects radiation transmitted through an object to be inspected is provided in the housing 21. Further, a control substrate 26, a case 28, a gate line driver 52, and a signal processing unit 54 are provided in the housing 21.

The radiation detector 20 comprises a scintillator 22 as an example of a light emitting layer that is irradiated with radiation and emits light, and a thin film transistor (TFT) substrate 30. Further, the scintillator 22 and the TFT substrate 30 are laminated in the order of the scintillator 22 and the TFT substrate 30 from the radiation incidence side. That is, the radiation detector 20 is a penetration side sampling (PSS) type radiation detector in which radiation is emitted from the scintillator 22 side. The scintillator 22 of the present embodiment contains gadolinium oxysulfide (GOS).

The case 28 and the gate line driver 52 are provided on the opposite lateral side of the radiation detector 20 from the control substrate 26 and the signal processing unit 54 with the radiation detector 20 interposed therebetween. The case 28 and the gate line driver 52, and the control substrate 26 and the signal processing unit 54 may be provided on the same lateral side of the radiation detector 20.

In the control substrate 26, electronic circuits such as an image memory 56, a controller 58, and a communication unit 66, which will be described later, are formed on the substrate. The case 28 houses a power supply unit 70 and the like, which will be described later.

Next, the configuration of a main part of an electrical system of the radiography apparatus 16 of the present embodiment will be described with reference to FIG. 3.

Figure 3:
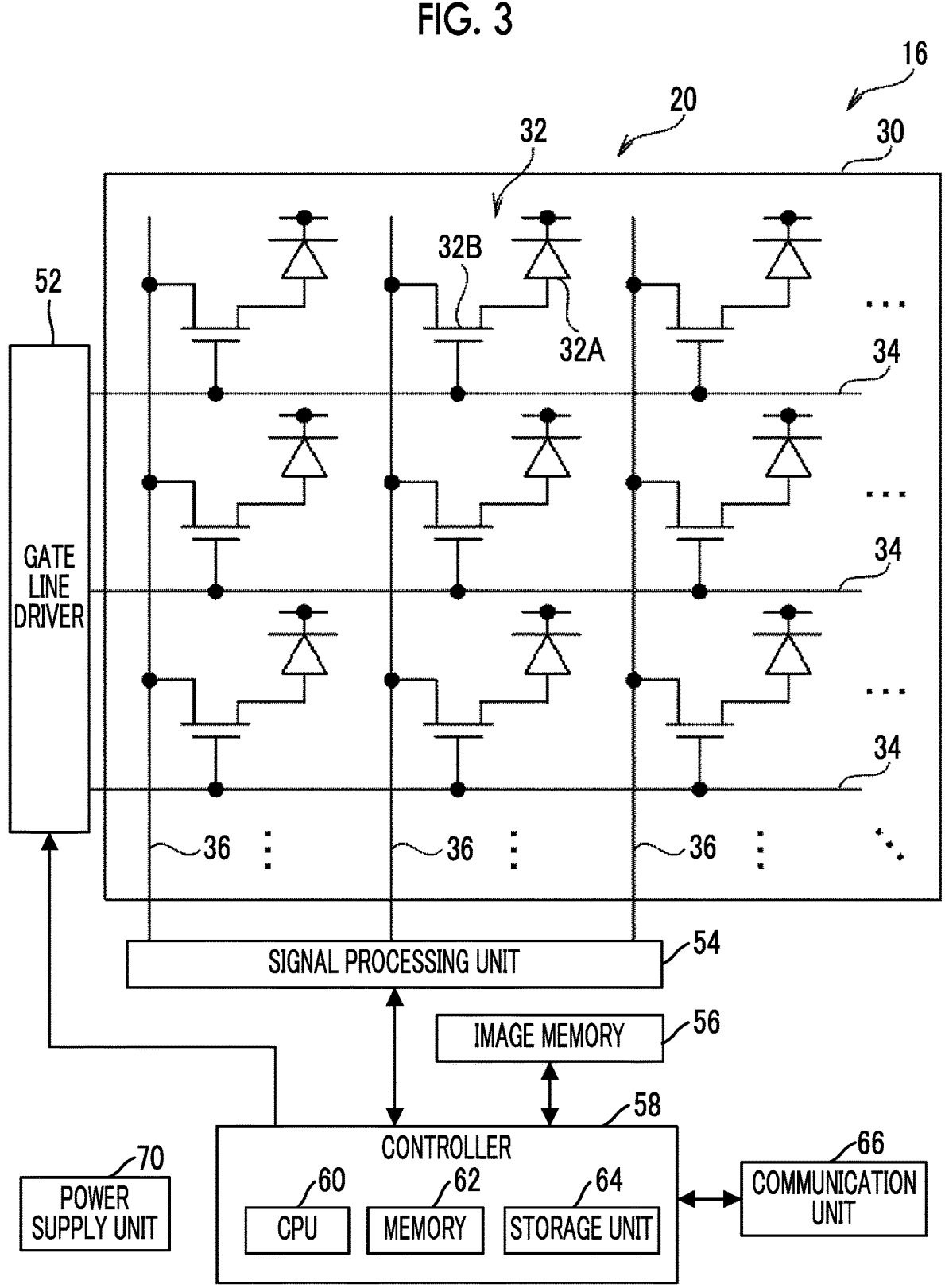
FIG. 3 is a block diagram showing an example of a configuration of a main part of an electrical system of the radiography apparatus of the embodiment.

As shown in FIG. 3, a plurality of pixels 32 are two-dimensionally provided on the TFT substrate 30 in one direction (a row direction in FIG. 3) and in a cross direction (a column direction in FIG. 3) intersecting the one direction. The pixel 32 includes a sensor unit 32A and a field-effect thin film transistor (TFT, hereinafter simply referred to as a "thin film transistor") 32B.

The sensor unit 32A includes, for example, an upper electrode, a lower electrode, and a photoelectric conversion film, which are not shown, absorbs the light emitted from the scintillator 22, generates electric charge, and accumulates the generated electric charge. The thin film transistor 32B converts the electric charge accumulated in the sensor unit 32A into an electrical signal and outputs the electrical signal. The sensor unit 32A is an example of a conversion element that generates a larger amount of electric charge as the dose of emitted radiation (hereinafter referred to as a "radiation dose") becomes larger. Further, the thin film transistor 32B is an example of a switching element that outputs the electric charge generated in the sensor unit 32A as an electrical signal.

A plurality of gate lines 34 which extend in the one direction and are used to turn each thin film transistor 32B on and off are provided on the TFT substrate 30. In addition, a plurality of data lines 36 which extend in the cross direction and are used to read out the electric charge via the thin film transistors 32B in an on state are provided on the TFT substrate 30. Each gate line 34 of the TFT substrate 30 is connected to the gate line driver 52 and each data line 36 of the TFT substrate 30 is connected to the signal processing unit 54.

The rows of the thin film transistors 32B of the TFT substrate 30 are sequentially turned on by the electrical signals which are supplied from the gate line driver 52 via the gate lines 34. Then, the electric charge read out by the thin film transistor 32B in an on state is transmitted as an electrical signal through the data line 36 and is received to the signal processing unit 54. In this way, the electric charge is sequentially read out from each row of the thin film transistors and image data showing a two-dimensional radiographic image is acquired.

The signal processing unit 54 comprises, for each data line 36, an amplifier circuit that amplifies the received electrical signal, and a sample-and-hold circuit (both not shown), and the electrical signal transmitted through each data line 36 is amplified by the amplifier circuit and is then held by the sample-and-hold circuit. A multiplexer and an analog-to-digital (AD) converter are connected to the output side of the sample-and-hold circuit in this order. The electrical signals held by each sample-and-hold circuit are sequentially (serially) received to the multiplexer and the electrical signals sequentially selected by the multiplexer are converted into digital image data by the AD converter.

The controller 58, which will be described later, is connected to the signal processing unit 54, and the image data output from the AD converter of the signal processing unit 54 is sequentially output to the controller 58. The image memory 56 is connected to the controller 58, the image data sequentially output from the signal processing unit 54 is sequentially stored in the image memory 56 under the control of the controller 58. The image memory 56 has storage capacity capable of storing a predetermined amount of image data, and each time a radiographic image is captured, the captured image data is sequentially stored in the image memory 56.

The controller 58 comprises a central processing unit (CPU) 60, a memory 62 including, for example, a read only memory (ROM) and a random access memory (RAM), and a non-volatile storage unit 64, such as a flash memory. An example of the controller 58 includes a microcomputer.

A communication unit 66 is connected to the controller 58 and transmits and receives various kinds of information to and from external apparatuses, such as the radiation irradiation apparatus 12 and the image processing apparatus 14, which will be described later, through wireless communication. The power supply unit 70 supplies power to each of the above-mentioned various circuits and elements, such as the gate line driver 52, the signal processing unit 54, the image memory 56, the controller 58, and the communication unit 66. In FIG. 3, in order to avoid complications, lines for connecting the power supply unit 70 to the various circuits and elements are not shown.

The base material of the TFT substrate 30 of the present embodiment is flexible, and is, for example, a resin sheet containing plastic, such as polyimide (PI). The thickness of the base material of the TFT substrate 30 may be a thickness capable of obtaining a desired flexibility according to the hardness of the material, the size of the TFT substrate 30, and the like. The thickness of the resin sheet may be, for example, 5 µm to 125 µm, more preferably 20 µm to 50 µm. Specific examples of the resin sheet include XENOMAX (registered trademark).

Figure 4:
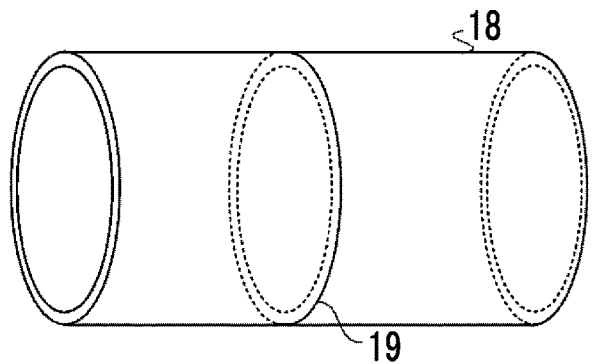
FIG. 4 is a diagram for explaining an object to be inspected and a portion to be inspected of the embodiment.
Figure 5:
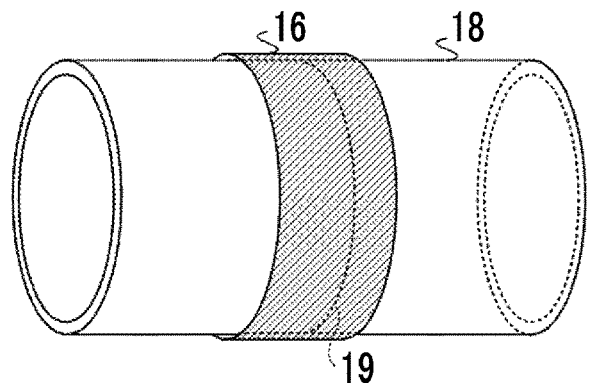
FIG. 5 is a diagram showing an example of a state in which the radiography apparatus of the embodiment is provided on the object to be inspected.

Further, the scintillator 22 and the portion of the housing 21 facing the detection surface of the radiation detector 20 of the present embodiment also have flexibility as in the TFT substrate 30. Therefore, as shown in FIG. 4 as an example, in a case where the object to be inspected 18 for the non-destructive inspection is, for example, a cylindrical object, such as a pipe of a natural gas pipeline, and the portion to be inspected 19 is a welded portion of two pipes, as shown in FIG. 5, the radiography apparatus 16 may be provided on the object to be inspected 18 in a state of being bent along the outer shape of the object to be inspected 18. In other words, the radiography apparatus 16 of the present embodiment may capture a radiographic image of the portion to be inspected 19 in a state of being wound around the object to be inspected 18.

In the present embodiment, the variation in sensitivity of the plurality of pixels 32 of the radiation detector 20 is corrected on the basis of the sensitivity correction image, before the portion to be inspected 19 is imaged. In the present embodiment, a radiographic image in which a portion different from the portion to be inspected 19 as a subject is imaged in a state in which the radiation detector 20 is wound around the object to be inspected 18, in other words, a radiographic image captured in a state of absence of the subject is used as the sensitivity correction image. Further, examples of a method of correcting the variation in sensitivity of the plurality of pixels 32 of the radiation detector 20 include gain correction. The correction for the variation in sensitivity of the plurality of pixels 32 of the radiation detector 20 may be performed by the radiography apparatus 16 or the image processing apparatus 14.

Figure 6:
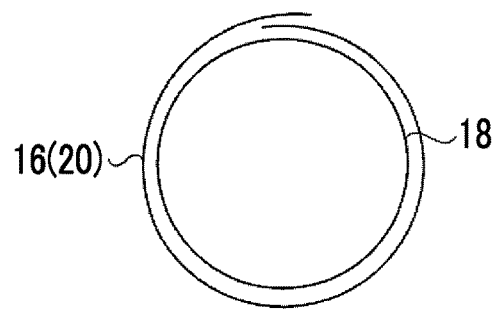
FIG. 6 is a cross-sectional view schematically showing an example of a cross-section of the object to be inspected around which the radiography apparatus of the embodiment is wound.

FIG. 6 shows a cross-sectional view schematically showing a cross-section of the object to be inspected 18 around which the radiography apparatus 16 is wound. In FIG. 6, the thicknesses of the radiography apparatus 16 and the object to be inspected 18 are ignored for the sake of simplification of the drawing. As shown in FIG. 6, in a case where the radiography apparatus 16 is wound around the object to be inspected 18, the end parts of the radiography apparatus 16 overlap with each other in many cases. In this case, the end parts of the radiation detector 20 of the radiography apparatus 16 also overlap with each other. In a case where the radiography apparatus 16 is irradiated with radiation from the radiation irradiation apparatus 12 in a state in which the end parts of the radiation detector 20 overlap with each other, to capture the radiographic image, the radiographic image subjected to the influence caused by the overlapping of the end parts is captured.

Figure 7:
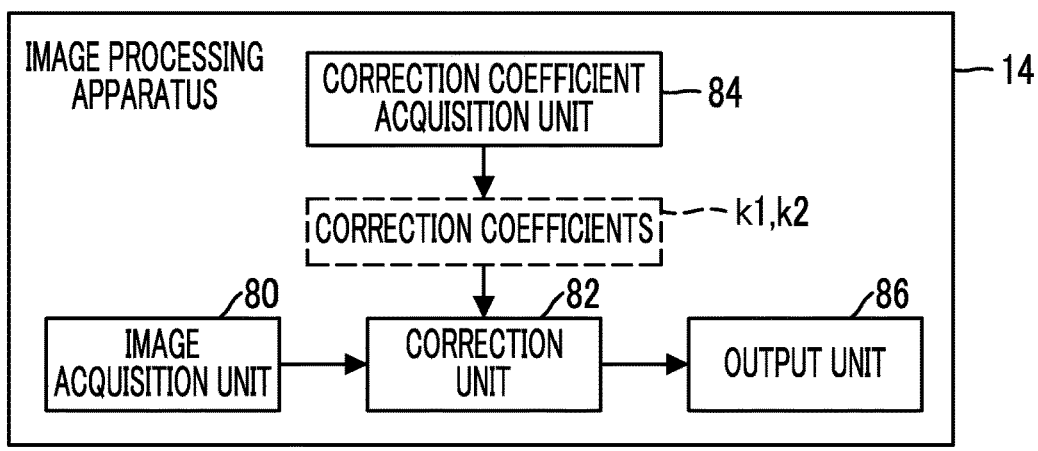
FIG. 7 is a block diagram showing an example of a functional configuration of an image processing apparatus of the embodiment.

Next, the functional configuration of the image processing apparatus 14 of the present embodiment will be described with reference to FIG. 7. As shown in FIG. 7, the image processing apparatus 14 comprises an image acquisition unit 80, a correction unit 82, a correction coefficient acquisition unit 84, and an output unit 86.

The image acquisition unit 80 acquires image data representing the radiographic image generated by the radiography apparatus 16.

Specifically, in the radiography system 10 of the present embodiment, the inspector who performs the non-destructive inspection first winds the radiography apparatus 16 around the portion to be inspected 19 of the object to be inspected 18 along the outer shape of the object to be inspected 18. Further, the inspector disposes the radiation irradiation apparatus 12 at a position corresponding to the portion provided with the radiography apparatus 16 inside the portion to be inspected 19 of the object to be inspected 18. For this disposition, for example, an electric trolley is used.

Next, the inspector operates the image processing apparatus 14 to input an instruction on capturing the radiographic image. When the capturing instruction is input, the image processing apparatus 14 transmits imaging conditions, such as a tube voltage, a tube current, and an irradiation period of radiation, to the radiation irradiation apparatus 12 and the radiography apparatus 16.

Radiation in accordance with the imaging conditions is emitted from the radiation source 13 of the radiation irradiation apparatus 12. Then, the image data according to the dose of radiation which has reached the radiation detector 20 of the radiography apparatus 16 is generated by the radiation detector 20. The image data generated by the radiation detector 20 is transmitted to the image processing apparatus 14 via the communication unit 66. The image acquisition unit 80 acquires the image data transmitted in this way from the radiography apparatus 16.

The correction unit 82 corrects the influence caused by the overlapping of the end parts of the radiation detector 20, which is included in the radiographic image represented by the image data acquired by the image acquisition unit 80, through image processing. As an example, the correction unit 82 of the present embodiment corrects the image data acquired by the image acquisition unit 80 by using the correction coefficients k1 and k2. Hereinafter, a method of correcting the image data by the correction unit 82 will be described with reference to FIGS. 8 and 9.

Figure 8:
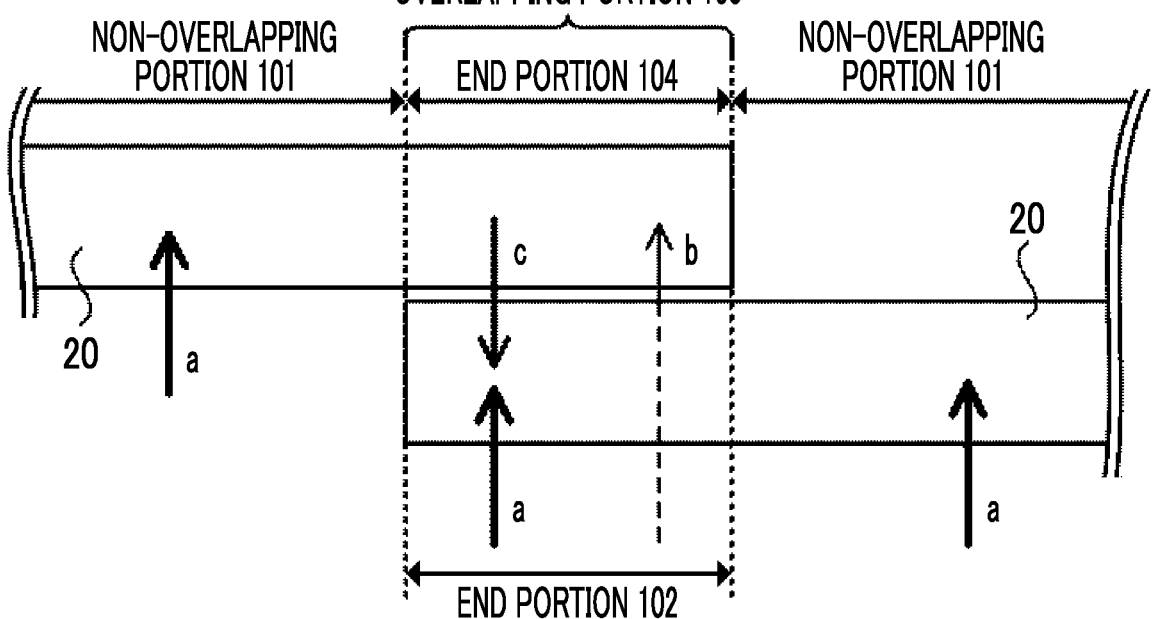
FIG. 8 is a diagram for explaining a method of correcting a radiographic image by a correction unit of the image processing apparatus.
Figure 9:
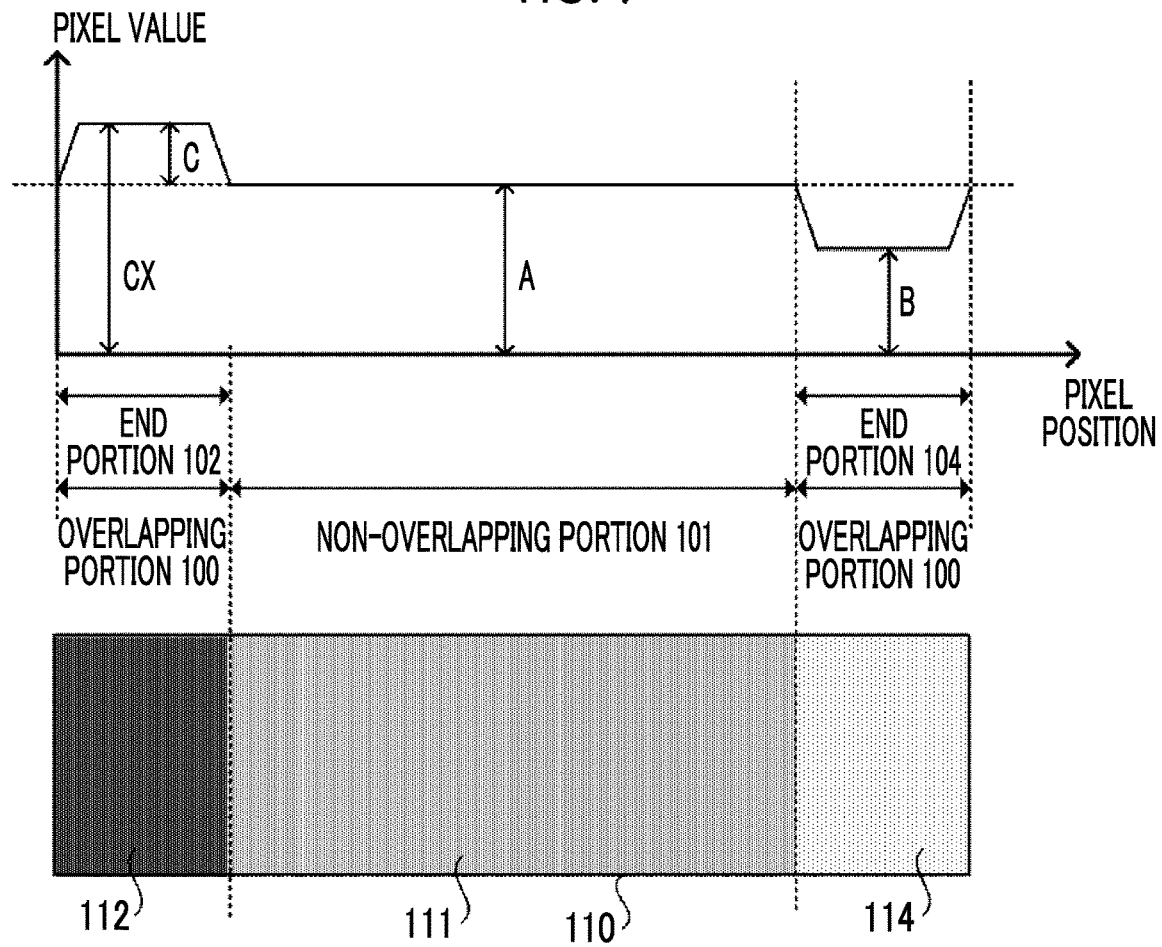
FIG. 9 is a diagram for explaining the method of correcting the radiographic image by the correction unit of the image processing apparatus.

FIG. 8 shows a diagram for explaining the dose of radiation emitted to the radiation detector 20 in a state in which the end parts of the radiation detector 20 overlap with each other. Further, FIG. 9 shows a graph representing the pixel value of a radiographic image 110 generated by the radiation detector 20 shown in FIG. 8 and an example of the radiographic image 110. The horizontal axis of the graph in FIG. 9 represents the pixel position of the radiation detector 20 along the outer peripheral direction of the object to be inspected 18, and the vertical axis represents the pixel value of the radiographic image 110.

As an example, a case where the radiography system 10 of the present embodiment performs the non-destructive inspection in a state in which the radiation irradiation apparatus 12 is disposed inside the object to be inspected 18 will be described. In a case where the radiation irradiation apparatus 12 is provided inside the object to be inspected 18, the radiation source 13 that emits radiation R is disposed at the center position in the cross-section of the object to be inspected 18 along the radial direction. Therefore, the dose of radiation a that reaches the detection surface of the radiation detector 20 facing the object to be inspected 18 is constant regardless of the position of the radiation detector 20 along the outer peripheral direction of the object to be inspected 18 in a case where the object to be inspected 18 has no defects, such as scratches.

More specifically, together with the overlapping portion 100 and the non-overlapping portion 101, the detection surface of the radiation detector 20 facing the object to be inspected 18 is irradiated with the same dose of the radiation a. Therefore, as shown in FIG. 9, the pixel value (density) of an image 111 of the region of the radiation detector 20 corresponding to the non-overlapping portion 101 is a pixel value A according to the dose of the radiation a.

On the other hand, as shown in FIG. 8, the radiation a is attenuated because the radiation is absorbed by the end portion 102 on the close side to the radiation source 13, and in the overlapping portion 100 of the radiation detector 20, the dose of radiation b that reaches the end portion 104 on the far side from the radiation source 13 is smaller than the dose of the radiation a. Therefore, as shown in FIG. 9, the pixel value of the image 114 of the region of the radiation detector 20 corresponding to the end portion 104 is a pixel value B according to the dose of the radiation b. The pixel value B is a value smaller than the pixel value A. In the radiographic image in the non-destructive inspection, since the image is whiter as the pixel value is smaller, the image 114 is a whiter image than the image 111.

As described above, there is an influence that the image 114 of the region of the radiation detector 20 corresponding to the end portion 104 has a pixel value smaller than the image 111 of the region corresponding to the non-overlapping portion 101 due to the end portion 102 of the radiation detector 20 imaged onto the image 114.

On the other hand, as shown in FIG. 8, in the overlapping portion 100 of the radiation detector 20, the end portion 102 on the close side to the radiation source 13 is irradiated with scattered radiation generated by the end portion 104, so-called backscattered radiation c, in addition to the radiation a emitted from the radiation source 13. Therefore, as shown in FIG. 9, the pixel value of the image 112 of the region of the radiation detector 20 corresponding to the end portion 102 is a value (pixel value CX) obtained by adding the pixel value A according to the dose of the radiation a and the pixel value C according to the dose of the backscattered radiation c. The pixel value CX is a value larger than the pixel value A. In the radiographic image in the non-destructive inspection, since the image is whiter as the pixel value is smaller, the image 112 is a blacker image than the image 111.

As described above, there is an influence that the image 112 of the region of the radiation detector 20 corresponding to the end portion 102 has a pixel value larger than the image 111 of the region corresponding to the non-overlapping portion 101 due to the influence of the backscattered radiation c caused by the end portion 104 of the radiation detector 20.

In a case where there are no influences of the radiation absorption (attenuation) caused by the end portion 102 and the backscattered radiation c (hereinafter, referred to as an "influence between the end parts of the radiation detector 20") as described above, the radiation emitted to both the end portions 102 and 104 is the radiation a. Therefore, in a case where there is no influence between the end parts of the radiation detector 20, the pixel value of the image 112 of the region corresponding to the end portion 102 and the pixel value of the image 114 of the region corresponding to the end portion 104 are the same.

The correction coefficient for correcting the influence of the end portion 104 on the end portion 102 is k1. In a case where there is no influence between the end parts of the radiation detector 20, as shown in Equation (1), a value obtained by adding the pixel value CX of the image 112 of the region corresponding to the end portion 102 and the pixel value B of the image 114 of the region corresponding to the end portion 104 should be twice the pixel value A of the image 111 of the region corresponding to the non-overlapping portion 101. In other words, a half value of the value obtained by adding the pixel value CX and the pixel value B should match the pixel value A.

$$(CX+B)/2 \rightarrow A \qquad (1)$$

Therefore, the correction coefficient k1 for correcting the image 112 is obtained by Equation (2).

$$k1=(CX+B)/2A \qquad (2)$$

The correction unit 82 of the image processing apparatus 14 of the present embodiment multiplies the pixel value of the image 112 of the end portion 102 by the correction coefficient k1 to correct the image 112 of the end portion 102.

On the other hand, the correction coefficient for correcting the influence of the end portion 102 on the end portion 104 is k2. The correction coefficient k2 is for compensating for the attenuation of radiation caused by the end portion 102, and since the relationship of Equation (3) is valid, the correction coefficient k2 for correcting the image 114 can be obtained by Equation (4).

$$k2 \times B \rightarrow A \qquad (3)$$

$$k2=A/B \qquad (4)$$

The correction unit 82 of the image processing apparatus 14 of the present embodiment multiplies the pixel value of the image 114 of the end portion 104 by the correction coefficient k2 to correct the image 114 of the end portion 104.

The correction coefficient acquisition unit 84 of the image processing apparatus 14 acquires the correction coefficients k1 and k2 that are used to correct the radiographic image by the correction unit 82.

As the method by which the correction coefficient acquisition unit 84 of the present embodiment acquires the correction coefficients k1 and k2, the following two methods are mainly used.

Figure 10:
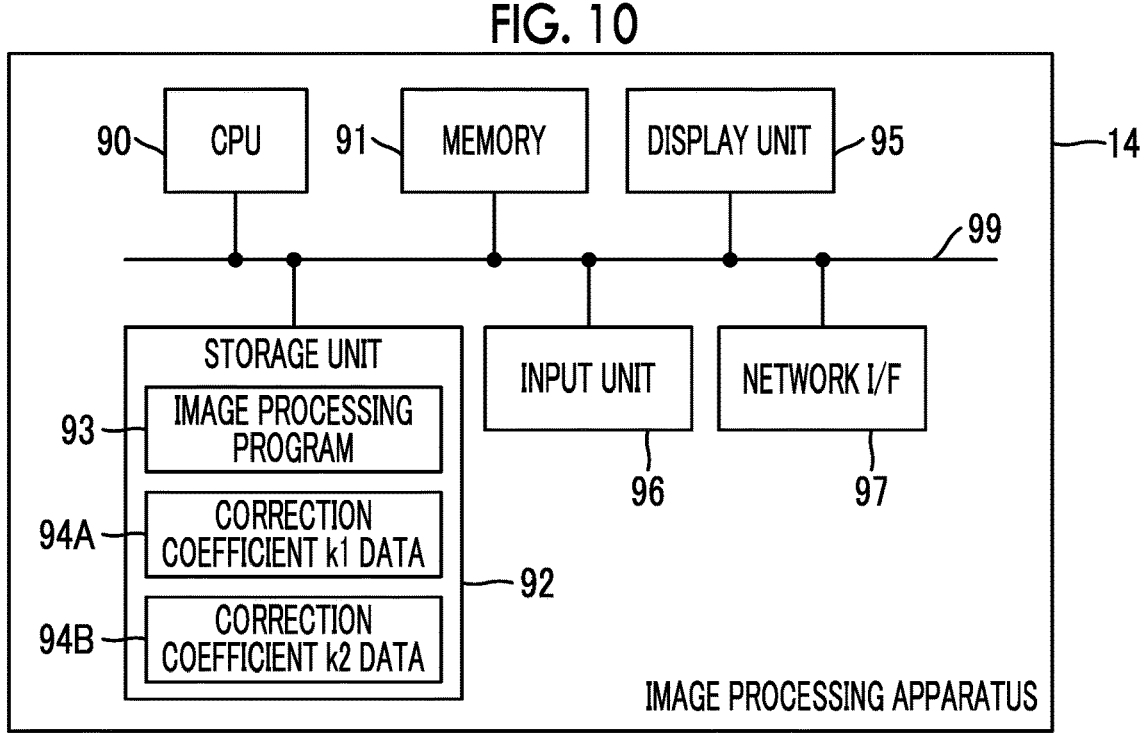
FIG. 10 is a block diagram showing an example of a hardware configuration of the image processing apparatus of the embodiment.

In the image processing apparatus 14 of the present embodiment, a first example of the methods includes a method of reading out the stored correction coefficient k1 data 94A representing the correction coefficient k1 and the stored correction coefficient k2 data 94B representing the correction coefficient k2 because the data is stored in the storage unit 92, as will be described later (see FIG. 10). The correction coefficient k1 data 94A and the correction coefficient k2 data 94B are stored in advance in the storage unit 92 on the basis of the correction coefficients k1 and k2 derived by, for example, an experiment or a simulation.

The dose of the backscattered radiation c caused by the end portion 104 and the amount of the radiation attenuation (absorption) caused by the end portion 102 are determined according to the material of the radiation detector 20 and the like. Therefore, the dose of the backscattered radiation c caused by the end portion 104 and the amount of the radiation attenuation (absorption) caused by the end portion 102 may vary depending on the type of radiation detector 20 used. In other words, the correction coefficients k1 and k2 may vary depending on the type of the radiation detector 20. In such a case, it is preferable to hold the correction coefficient k1 data 94A and the correction coefficient k2 data 94B in association with the type of the radiation detector 20.

Alternatively, the dose of the backscattered radiation c and the amount of the radiation attenuation (absorption) caused by the end portion 102 may vary depending on the size (area) of the overlapping portion 100. In other words, the correction coefficients k1 and k2 may vary depending on the size of the overlapping portion 100. In such a case, it is preferable to hold the correction coefficient k1 data 94A and the correction coefficient k2 data 94B in association with the size of the overlapping portion 100.

Further, a second example of the methods includes a method in which the correction coefficient acquisition unit 84 derives the correction coefficient k1 from the image data of the radiographic image for correction (hereinafter, referred to as a "correction image") by using Equation (2), and also derives the correction coefficient k2 by using Equation (4). In this case, a radiographic image captured by the radiation detector 20 in a state in which the radiography apparatus 16 is bent in a tubular shape as in a case where the non-destructive inspection is performed in a state of absence of the subject, such as the object to be inspected 18, may be used as the correction image. Alternatively, for example, a radiographic image in which a portion of the object to be inspected 18 different from the portion to be inspected 19 is imaged may be used as a correction image.

By which method the correction coefficient acquisition unit 84 acquires the correction coefficient may be predetermined according to the imaging instruction or the like, or may be instructed by the inspector through the input unit 96.

The output unit 86 outputs image data corrected by the correction unit 82 to the display unit 95, which will be described later.

Next, the hardware configuration of the image processing apparatus 14 of the present embodiment will be described with reference to FIG. 10. As shown in FIG. 10, the image processing apparatus 14 includes a CPU 90, a memory 91 as a temporary storage area, and a non-volatile storage unit 92. Further, the image processing apparatus 14 includes a display unit 95, such as a liquid crystal display, an input unit 96, such as a keyboard, and a network interface (I/F) 97 that controls wireless communication. The CPU 90, the memory 91, the storage unit 92, the display unit 95, the input unit 96, and the network I/F 97 are connected to a bus 99.

The storage unit 92 is implemented by a hard disk drive (HDD), a solid state drive (SSD), a flash memory, or the like. The image processing program 93, the above-mentioned correction coefficient k1 data 94A, and the above-mentioned correction coefficient k2 data 94B are stored in the storage unit 92 as a storage medium. The CPU 90 reads out the image processing program 93 from the storage unit 92, extracts the program to the memory 91, and executes the extracted image processing program 93. The CPU 90 executes the image processing program 93 to function as the image acquisition unit 80, the correction unit 82, the correction coefficient acquisition unit 84, and the output unit 86 shown in FIG. 7.

Next, the operation of the image processing apparatus 14 of the present embodiment will be described with reference to FIGS. 11 and 12. The CPU 90 executes the image processing program 93, whereby the image processing shown in FIG. 11 is executed.

Figure 11:
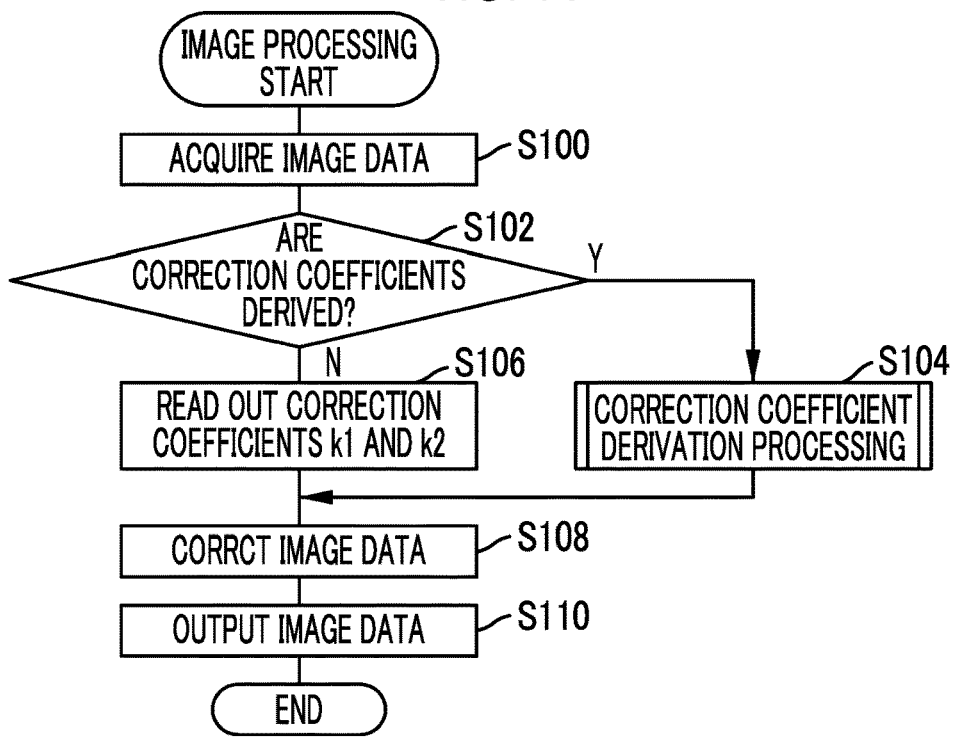
FIG. 11 is a flowchart showing an example of image processing that is executed by the image processing apparatus of the embodiment.

The image processing shown in FIG. 11 is executed, for example, in a case where the inspector inputs an instruction on capturing the radiographic image via the input unit 96. As described above, in response to the capturing instruction, radiation R is emitted from the radiation source 13, and the image data is transmitted from the radiography apparatus 16 to the image processing apparatus 14.

In Step S100 of FIG. 11, the image acquisition unit 80 acquires the image data transmitted from the radiography apparatus 16. In next Step S102, the correction coefficient acquisition unit 84 determines whether or not to derive the correction coefficients k1 and k2. As described above, in a case where the correction coefficient acquisition unit 84 derives the correction coefficients, the determination in Step S102 is affirmative, and the process proceeds to Step S104.

Figure 12:
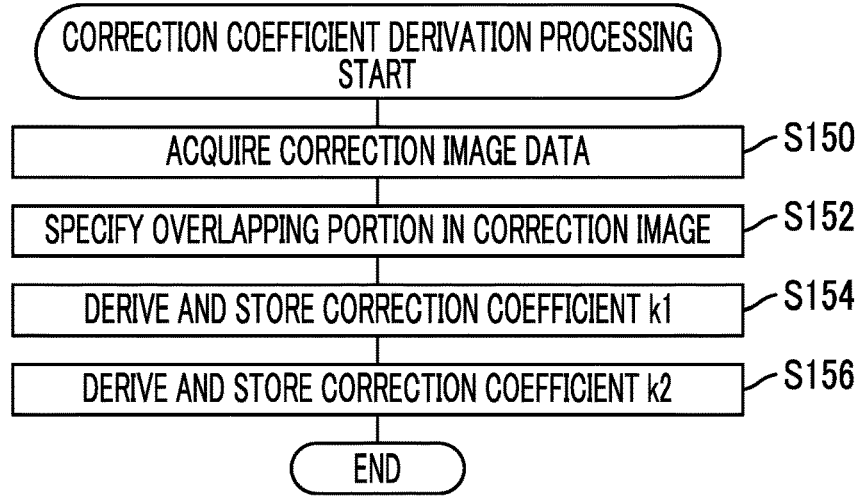
FIG. 12 is a flowchart showing an example of correction coefficient derivation processing that is executed in the image processing shown in FIG. 11.

In step S104, the correction coefficient acquisition unit 84 executes correction coefficient derivation processing shown in FIG. 12. In Step S150 of FIG. 12, the correction coefficient acquisition unit 84 acquires the image data of the correction image (hereinafter, referred to as "correction image data"). The correction image data corresponds to the image data of the radiographic image 110 described above. In a case where the correction image data is stored in the storage unit 92 or the like in advance, the correction coefficient acquisition unit 84 reads out the correction image data from the storage unit 92, to acquire the correction image data.

Further, in a case where a part of the region of the radiographic image represented by the image data acquired in Step S100 of the image processing is used as the correction image, the correction coefficient acquisition unit 84 acquires the image data corresponding to the region that is used as the correction image from the radiographic image, as the correction image data. For example, in a case where the radiographic image includes an image area that does not include the object to be inspected 18, such as a case where the end portion of the object to be inspected 18 is imaged, the image area that does not include the object to be inspected 18 may be used as the correction image. Alternatively, for example, in a case where the radiography apparatus 16 (radiation detector 20) is larger than the portion to be inspected 19 and the radiographic image includes a region that can be said to be an image that does not depend on the portion to be inspected 19, the region may be used as the correction image.

In next Step S152, the correction coefficient acquisition unit 84 specifies the overlapping portion 100 in the correction image represented by the correction image data. The method by which the correction coefficient acquisition unit 84 specifies the overlapping portion 100 is not particularly limited. For example, in a case where the correction unit 82 corrects the image data in Step S108 of the image processing, which will be described later, the same method as the method of specifying the overlapping portion 100 may be applied.

In next Step S154, the correction coefficient acquisition unit 84 derives the correction coefficient k1 and makes the storage unit 92 or the like temporarily store the correction coefficient k1. Specifically, the correction coefficient acquisition unit 84 specifies the end portions 102 and 104 and the non-overlapping portion 101 on the basis of the overlapping portion 100 specified in Step S152. Further, as described above, the correction coefficient k1 is derived by Equation (2) using the pixel value CX of the image 112 of the end portion 102, the pixel value B of the image 114 of the end portion 104, and the pixel value A of the image 111 of the non-overlapping portion 101.

In next Step S156, the correction coefficient acquisition unit 84 derives the correction coefficient k2 and makes the storage unit 92 or the like temporarily store the correction coefficient k2. Specifically, as described above, the correction coefficient acquisition unit 84 derives the correction coefficient k2 by Equation (4) using the pixel value B of the image 114 of the end portion 104 and the pixel value A of the image 111 of the non-overlapping portion 101. When the processing of Step S156 ends, the correction coefficient derivation processing ends. Then, the process proceeds to Step S108 of the image processing shown in FIG. 11.

On the other hand, in a case where the correction coefficient acquisition unit 84 does not derive the correction coefficients k1 and k2, the determination in Step S102 is negative, and the process proceeds to Step S106. In Step S106, the correction coefficient acquisition unit 84 reads out the correction coefficient k1 from the correction coefficient k1 data 94A of the storage unit 92, and reads out the correction coefficient k2 from the correction coefficient k2 data 94B.

In next Step S108, the correction unit 82 corrects the image data acquired in Step S100, as described above, by using the correction coefficients k1 and k2. In the present embodiment, the correction unit 82 first specifies the overlapping portion 100 in the radiographic image represented by the image data, more specifically, each of the end portions 102 and 104.

The method by which the correction unit 82 specifies each of the end portions 102 and 104 in the radiographic image is not particularly limited. In a case where a metal marker or the like representing the overlapping portion is imaged together with the portion to be inspected 19 in the imaging of the object to be inspected 18, the correction unit 82 may specify the end portions 102 and 104 on the basis of the image of the marker or the like. Alternatively, for example, as described above, since the pixel values of the non-overlapping portion 101 and the overlapping portion 100 are different from each other, a line image is generated at the boundary portion between the overlapping portion 100 and the non-overlapping portion 101. Therefore, the correction unit 82 may specify the end portions 102 and 104 according to the positional relationship with the line image and the magnitude of the pixel value by detecting the line image serving as the boundary portion.

Alternatively, in a case where the object to be inspected 18 is, as described above, a pipe for a natural gas pipeline or the like, since the diameter of the object to be inspected 18 is predetermined, the length (size) of the non-overlapping portion 101 is predetermined. The length (size) and the position of the end portions 102 and 104 are uniquely determined by the length (size) of the non-overlapping portion 101. Therefore, the correction unit 82 may specify the end portions 102 and 104 according to the diameter of the object to be inspected 18 and the like.

In a case where the end portions 102 and 104 are specified in this way, the correction unit 82 multiplies the pixel value of the image 112 of the end portion 102 by the correction coefficient k1 as described above to correct the image 112 of the end portion 102. Further, as described above, the correction unit 82 multiplies the pixel value of the image 114 of the end portion 104 by the correction coefficient k2 to correct the image 114 of the end portion 104.

In next Step S110, the output unit 86 outputs the image data corrected by the processing of Step S108 to the display unit 95. By the processing of Step S110, the corrected radiographic image is displayed on the display unit 95. The inspector visually confirms the radiographic image displayed on the display unit 95 to grasp the presence or absence of defects in the portion to be inspected 19 of the object to be inspected 18. When the processing of Step S110 ends, the image processing ends.

As described above, the image processing apparatus 14 of the present embodiment comprises an image acquisition unit 80 that acquires, from a radiation detector 20 in which a plurality of pixels 32 each of which outputs an electrical signal according to a dose of radiation R emitted from a radiation source 13 are arranged, a radiographic image captured in a state in which the end parts of the radiation detector 20 overlap with each other; and a correction unit 82 that corrects an influence of the end portion 104 on a far side from the radiation source 13, which is included in the radiographic image.

Accordingly, with the image processing apparatus 14 of the present embodiment, the radiographic image can be accurately corrected.

In general, the dose of the radiation R emitted from the radiation source 13 in a case of performing the non-destructive inspection is relatively larger than the dose of radiation emitted from a radiation source that is used to image a patient or the like for medical purposes. Therefore, in a case where the image is captured in a state in which the end parts of the radiation detector 20 overlap with each other, the dose of the backscattered radiation c caused by the end portion 104 of the overlapping portion 100 far from the radiation source 13 increases as compared with the radiographic image for medical purposes. Accordingly, the radiographic image in the non-destructive inspection is an image subjected to the influence of the backscattered radiation as compared with the radiographic image for medical purposes.

Therefore, in a case where the image processing apparatus 14 of the present embodiment is applied to the correction of the radiographic image in the non-destructive inspection, a higher effect can be obtained.

Further, in the present embodiment, before the portion to be inspected 19 is imaged, the variation in sensitivity of the plurality of pixels 32 of the radiation detector 20 can be corrected on the basis of the sensitivity correction image, in a state in which the radiation detector 20 is wound around the object to be inspected 18. Therefore, the variation in sensitivity of the plurality of pixels 32 can be corrected more appropriately, and the image quality of the captured radiographic image can be improved.

In the present embodiment, an aspect in which the correction unit 82 of the image processing apparatus 14 corrects both the image 112 of the end portion 102 and the image 114 of the end portion 104 has been described, but the present disclosure is not limited to the present embodiment. Since the image 112 and the image 114 are images corresponding to the same portion of the object to be inspected 18, an aspect in which the correction unit 82 corrects either one may be employed. In this case, it is preferable to employ an aspect in which the image of the radiation detector 20 close to the object to be inspected 18, the image 112 of the end portion 102 in the present embodiment, is corrected. In this case, the correction coefficient acquisition unit 84 may acquire only the correction coefficient k1.

In the present embodiment, an aspect in which the correction unit 82 of the image processing apparatus 14 corrects the images 112 and 114 of the overlapping portion 100 in the radiographic image 110 by using the correction coefficients k1 and k2 has been described, but the correction method is not limited to the aspect in which the correction coefficients k1 and k2 are used. For example, an aspect in which the same correction equation is used instead of the correction coefficients k1 and k2 may be employed as the correction method. Further, for example, in a case where the influence of the backscattered radiation c is removed from the image 112 of the end portion 102, an aspect in which a filter having a frequency according to the backscattered radiation c is applied to the image 112 may be employed as the correction method.

Figure 13:
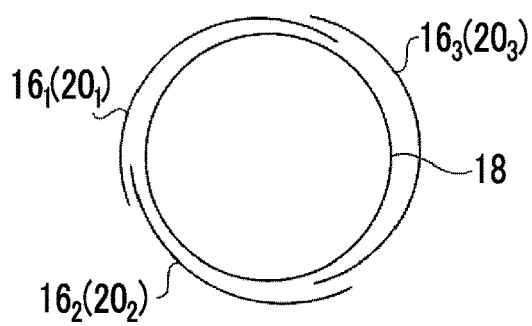
FIG. 13 is a diagram showing an example of a state in which a plurality of the radiography apparatuses of the embodiment are provided on the object to be inspected.

Further, in the present embodiment, an aspect in which one radiography apparatus 16 (radiation detector 20) images the object to be inspected 18 has been described, but a plurality of the radiography apparatuses 16 (radiation detectors 20) that are used to image the object to be inspected 18 may be used. As an example, an aspect in which the object to be inspected 18 is imaged by using three radiography apparatuses $16_1$ to $16_3$ (radiation detectors $20_1$ to $20_3$) is shown. As shown in FIG. 13, in a case where the radiography apparatus $16_1$ to $16_3$ are used, each of the radiography apparatuses $16_1$ to $16_3$ is disposed in a state in which the end parts of the adjacent radiography apparatuses $16_1$ to $16_3$ overlap with each other, and wound around the object to be inspected 18.

Accordingly, the overlapping portion 100 and the non-overlapping portion 101 are present in the radiographic image captured by each of the radiation detectors $20_1$ to $20_3$ of the radiography apparatuses $16_1$ to $16_3$, as in the radiographic image 110 as described above, but with the image processing apparatus 14 of the present embodiment, the radiographic image can be accurately corrected.

Further, at least a part of the image processing shown in FIG. 11 executed by the CPU 90 of the image processing apparatus 14 in the present embodiment may be executed by the CPU 60 of the radiography apparatus 16.

Further, in the present embodiment, the case where the PSS type radiation detector in which the radiation is emitted from the scintillator 22 side is applied to the radiation detector 20 has been described, but the present disclosure is not limited thereto. For example, an aspect in which an irradiation side sampling (ISS) type radiation detector in which radiation is emitted from the TFT substrate 30 side is applied to the radiation detector 20 may be employed.

Further, in the present embodiment, the case where an indirect conversion type radiation detector that temporarily converts radiation into light and then converts the converted light into electric charge is applied to the radiation detector 20 has been described, but the present disclosure is not limited thereto. For example, an aspect in which a direct conversion type radiation detector that directly converts radiation into electric charge is applied to the radiation detector 20 may be employed.

Further, in the present embodiment, for example, as a hardware structure of a processing unit that executes various processing such as processing performed by the image acquisition unit 80, the correction unit 82, the correction coefficient acquisition unit 84, and the output unit 86, the following various processors may be used. The various processors include, for example, a programmable logic device (PLD), such as a field programmable gate array (FPGA), which is a processor having a changeable circuit configuration after manufacture and a dedicated electrical circuit, such as an application specific integrated circuit (ASIC), which is a processor having a dedicated circuit configuration designed to perform specific processing, in addition to the CPU which is a general-purpose processor that executes software (program) to function as various processing units as described above.

One processing unit may be constituted of one of the various processors or may be constituted of a combination of two or more processors of the same type or different types (for example, a combination of a plurality of FPGAs and a combination of a CPU and an FPGA). Further, the plurality of processing units may constitute one processor.

A first example of the configuration in which the plurality of processing units are constituted of one processor is an aspect in which one or more CPUs and software are combined to constitute one processor and the processor functions as a plurality of processing units. A representative example of the aspect is a computer such as a client and server. A second example of the configuration is an aspect in which a processor that implements all of the functions of a system including the plurality of processing units with one integrated circuit (IC) chip is used. A representative example of the aspect is a system-on-chip (SoC). As such, the hardware structure of various processing units is formed by using one or more of the various processors.

Specifically, an electrical circuit (circuitry) obtained by combining circuit elements, such as semiconductor elements, may be used as the hardware structure of these various processors.

In the present embodiment, the aspect in which the image processing program 93 is stored (installed) in the storage unit 92 in advance has been described, but the present disclosure is not limited thereto. The image processing program 93 may be recorded on a recording medium, such as a compact disc read only memory (CD-ROM), a digital versatile disc read only memory (DVD-ROM), or a universal serial bus (USB) memory, and then provided. Further, the image processing program 93 may be downloaded from an external apparatus via the network.

EXPLANATION OF REFERENCES

10: radiography system
12: radiation irradiation apparatus
13: radiation source
14: image processing apparatus
16, 16₁ to 16₃: radiography apparatus
18: object to be inspected
19: portion to be inspected
20, 20₁ to 20₃: radiation detector
21: housing
22: scintillator
26: control substrate
28: case
30: TFT substrate
32: pixel
32A: sensor unit
32B: thin film transistor
34: gate line
36: data line
52: gate line driver
54: signal processing unit
56: image memory
58: controller
60, 90: CPU
62, 91: memory
64, 92: storage unit
66: communication unit
70: power supply unit
80: image acquisition unit
82: correction unit
84: correction coefficient acquisition unit
86: output unit
93: image processing program
94A: correction coefficient k1 data
94B: correction coefficient k2 data
95: display unit
96: input unit
97: network I/F
99: bus
100: overlapping portion
101: non-overlapping portion
102, 104: end portion
110: radiographic image
111, 112, 114: image
a, b, R: radiation
c: backscattered radiation
k1, k2: correction coefficient
A, B, C, CX: pixel value

What is claimed is:

1. An image processing apparatus comprising:
a processor configured to:
acquire, from a radiation detector in which a plurality of pixels each of which outputs an electrical signal according to a dose of radiation emitted from a radiation source are arranged, a radiographic image captured in a state in which the radiation detector is bent and one end part and the other end part of the radiation detector overlap with each other, the radiation detector being flexible; and
correct the radiographic image by correcting an influence of a portion of the radiographic image corresponding to the one end part close to the radiation source of the two end parts, due to backscattered radiation where the dose of radiation is scattered on the other end part far from the radiation source.

2. The image processing apparatus according to claim 1, wherein the processor corrects the influence on an image of an overlapping portion of the one end part and the other end part of the radiation detector in the radiographic image.

3. The image processing apparatus according to claim 1, the processor is further configured to:
acquire a sensitivity correction image captured by the radiation detector in a state of absence of a subject;
correct a sensitivity of the plurality of pixels of the radiation detector on a basis of a sensitivity correction image; and
acquire a correction coefficient obtained on a basis of the sensitivity correction image captured by the radiation detector in the state of absence of a subject,
wherein the correction of the influence includes correcting the radiographic image by using the correction coefficient.

4. The image processing apparatus according to claim 1,
wherein the radiographic image that the processor acquires is a radiographic image in which a portion to be inspected of a subject to be inspected is imaged,
the processor is further configured to acquire a correction coefficient obtained on a basis of a correction image in which a portion of the subject to be inspected different from the portion to be inspected is imaged by the radiation detector, and
the processor corrects the radiographic image by using the correction coefficient.

5. The image processing apparatus according to claim 1,
wherein the radiation detector includes a plurality of radiation detectors, and
wherein the processor acquires the radiographic image captured by each of the plurality of the radiation detectors arranged in a state in which the one end part and the other end part overlap with each other.

6. A radiography system comprising:
a radiation detector in which a plurality of pixels each of which outputs an electrical signal according to a dose of emitted radiation are arranged; and
the image processing apparatus according to claim 1.

7. The image processing apparatus according to claim 2, the processor is further configured to:
acquire a sensitivity correction image captured by the radiation detector in a state of absence of a subject;
correct a sensitivity of the plurality of pixels of the radiation detector on a basis of a sensitivity correction image; and
acquire a correction coefficient obtained on a basis of the sensitivity correction image captured by the radiation detector in the state of absence of a subject,
wherein the correction of the influence includes correcting the radiographic image by using the correction coefficient.

8. The image processing apparatus according to claim 2,
wherein the radiographic image that the processor acquires is a radiographic image in which a portion to be inspected of a subject to be inspected is imaged,
the processor is further configured to acquire a correction coefficient obtained on the basis of a correction image in which a portion of the subject to be inspected different from the portion to be inspected is imaged by the radiation detector, and
the processor corrects the radiographic image by using the correction coefficient.

9. The image processing apparatus according to claim 3,
wherein the processor derives the correction coefficient on a basis of a pixel value of an image of an overlapping portion of the one end part and the other end part of the radiation detector and a pixel value of an image of a non-overlapping portion of the radiation detector in the correction image.

10. The image processing apparatus according to claim 4,
wherein the processor derives the correction coefficient on a basis of a pixel value of an image of an overlapping portion of the one end part and the other end part of the radiation detector and a pixel value of an image of a non-overlapping portion of the radiation detector in the correction image.

11. The radiography system according to claim 6,
wherein each of the plurality of pixels includes a conversion element that generates a larger amount of electric charge as the dose of emitted radiation becomes larger, and a switching element that outputs the electric charge generated by the conversion element as the electrical signal.

12. An image processing method comprising:
acquiring, from a radiation detector in which a plurality of pixels each of which outputs an electrical signal according to a dose of radiation emitted from a radiation source are arranged, a radiographic image captured in a state in which the radiation detector is bent and one end part and the other end part of the radiation detector overlap with each other, the radiation detector being flexible; and
correcting the radiographic image by correcting an influence of a portion of the radiographic image corresponding to the one end part close to the radiation source, due to backscattered radiation where the dose of radiation is scattered on the other end part far from the radiation source.

13. A non-transitory computer readable recording medium storing an image processing program that causes a computer to execute a process comprising:
acquiring, from a radiation detector in which a plurality of pixels each of which outputs an electrical signal according to a dose of radiation emitted from a radiation source are arranged, a radiographic image captured in a state in which the radiation detector is bent and one end part and the other end part of the radiation detector overlap with each other, the radiation detector being flexible; and
correcting the radiographic image by correcting an influence of a portion of the radiographic image corresponding to the one end part close to the radiation source, due to backscattered radiation where the dose of radiation is scattered on the one end part far from the radiation source.

* * * * *